US00PP33411P2

(12) United States Plant Patent
Németh

(10) Patent No.: US PP33,411 P2
(45) Date of Patent: Aug. 31, 2021

(54) CHERRY LAUREL PLANT NAMED 'ZSÓFI'

(50) Latin Name: *Prunus laurocerasus*
Varietal Denomination: Zsófi

(71) Applicant: Gabor Péter Németh, Szombathely (HU)

(72) Inventor: Gabor Péter Németh, Szombathely (HU)

( * ) Notice: Subject to any disclaimer, the term of this patent is extended or adjusted under 35 U.S.C. 154(b) by 0 days.

(21) Appl. No.: 17/072,898

(22) Filed: Oct. 16, 2020

(51) Int. Cl.
*A01H 5/12* (2018.01)
*A01H 6/74* (2018.01)

(52) U.S. Cl.
USPC ..... Plt./226
CPC ..... *A01H 6/7427* (2018.05)

(58) Field of Classification Search
USPC ..... Plt./226
CPC ..... A01H 6/7427; A01H 5/12; A01H 5/00
See application file for complete search history.

*Primary Examiner* — Keith O. Robinson
(74) *Attorney, Agent, or Firm* — Weatherly IP Solutions, LLC; Barbara Campbell

(57) ABSTRACT

A new cherry laurel plant particularly distinguished by having a broad upright to spreading habit, a broad obovate plant shape, and a moderate growth rate, is disclosed.

2 Drawing Sheets

Genus and species: *Prunus laurocerasus.*
Variety denomination: 'Zsófi'.

BACKGROUND OF THE NEW PLANT

The present invention comprises a new and distinct variety of cherry laurel plant, botanically known as *Prunus laurocerasus*, and hereinafter referred to by the variety name 'Zsófi'. 'Zsófi' originated from an open-pollination conducted in Szombathely, Hungary in May 2009 between un-named and unpatented *Prunus laurocerasus* parent plants.

The seeds from the open-pollination were sown and plants were grown outdoors for evaluation, where an individual plant designated 'Zsófi' was selected from the group of plants in Szombathely, Hungary in May 2011. In October 2017, 'Zsófi' was first vegetatively propagated by softwood cuttings. 'Zsófi' was found to reproduce true to type in successive generations of asexual propagation via softwood cuttings.

SUMMARY

The following are the most outstanding and distinguishing characteristics of this new variety when grown under normal horticultural practices in The Netherlands.

1. A broad upright to spreading habit;
2. A broad obovate plant shape; and
3. A moderate growth rate.

DESCRIPTION OF THE PHOTOGRAPHS

This new cherry laurel plant is illustrated by the accompanying photographs which show the plant's overall plant habit including form, and foliage. The photographs are of a 28-month-old plant grown outdoors in The Netherlands and taken in September 2020. The colors shown are as true as can be reasonably obtained by conventional photographic procedures.

DESCRIPTION OF THE NEW VARIETY

Figure 1:
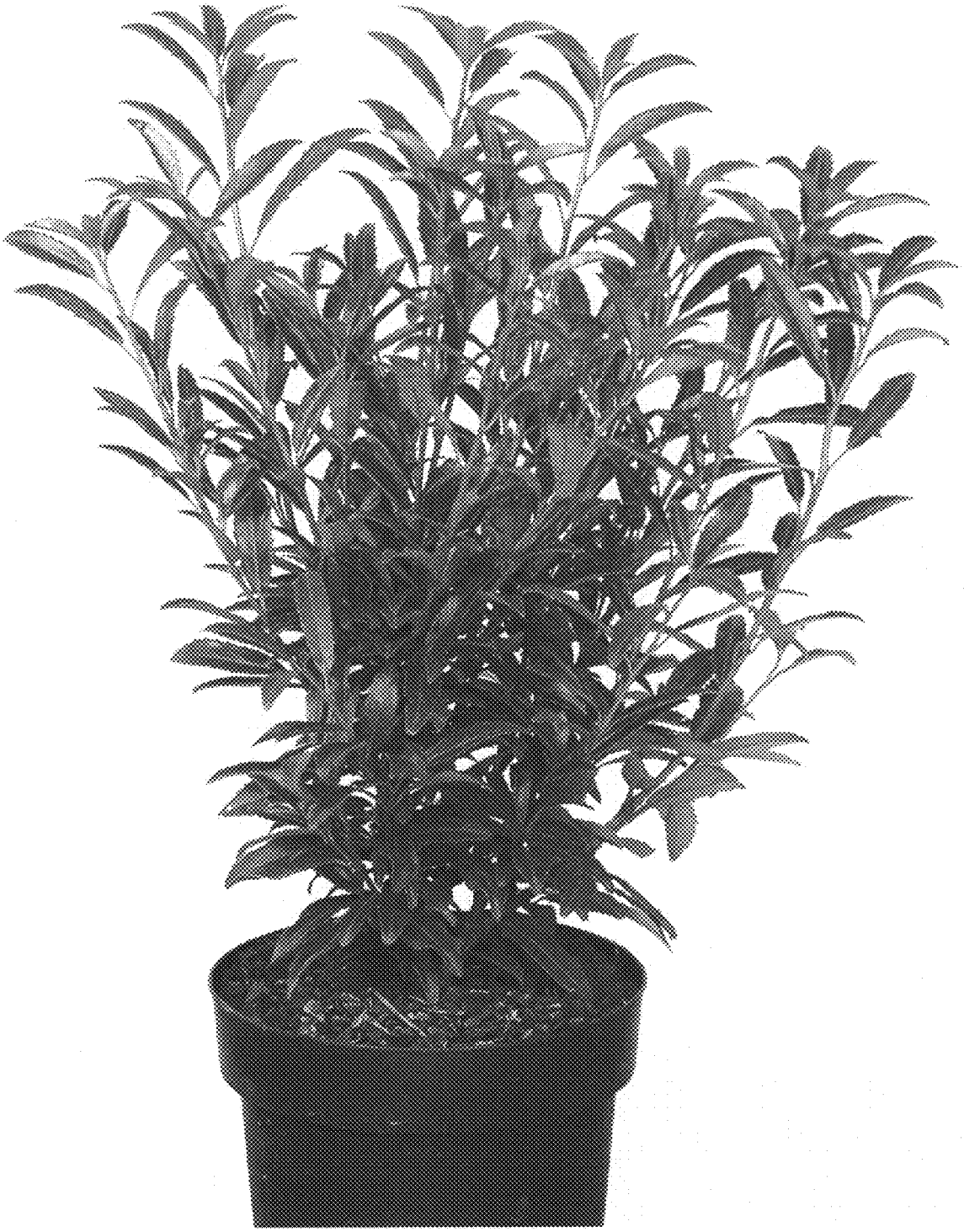
FIG. 1 shows the overall plant habit of 'Zsófi'.
Figure 2:
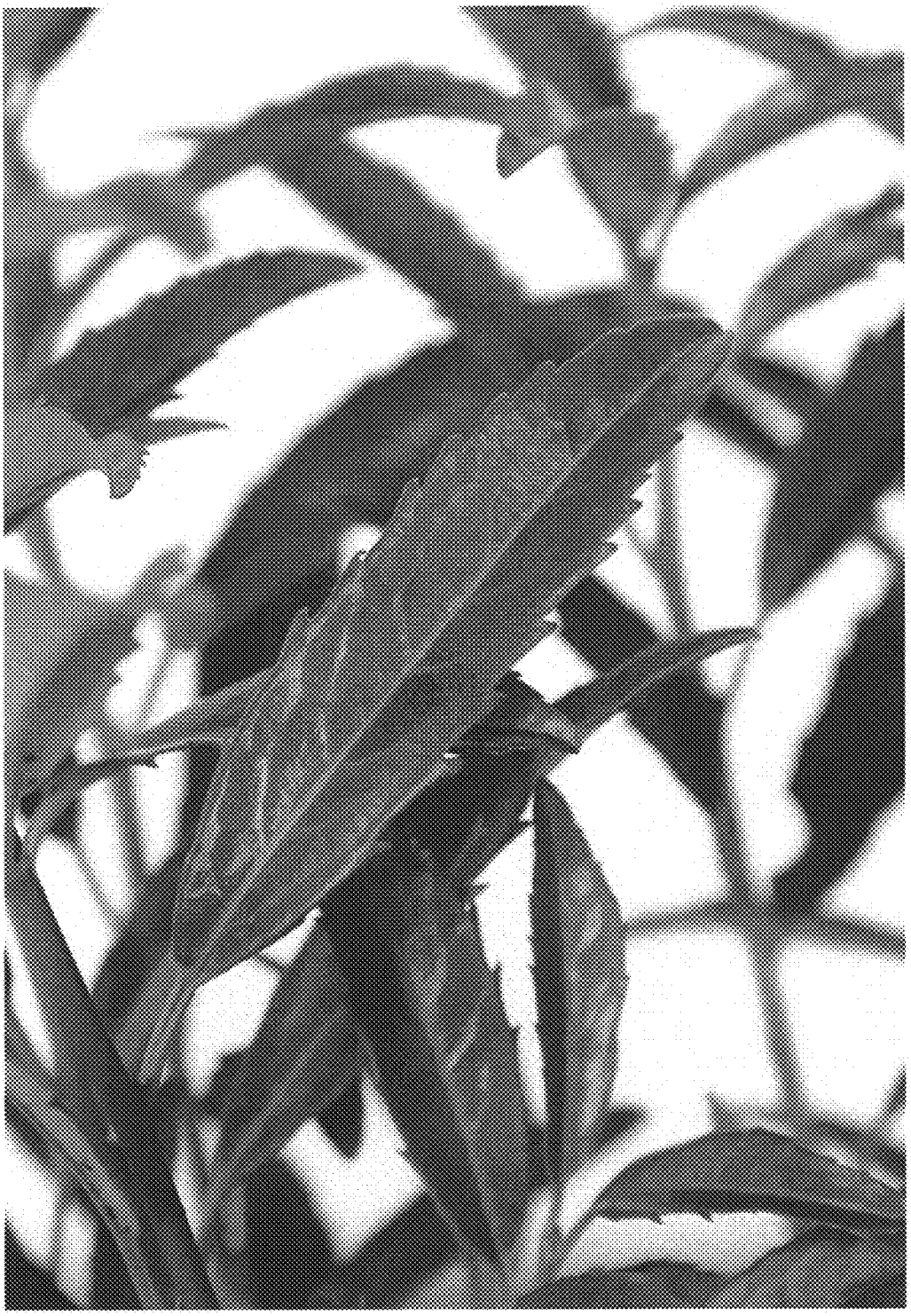
FIG. 2 shows a close-up of an individual leaf.

The following detailed descriptions set forth the distinctive characteristics of 'Zsófi'. The data which define these characteristics were collected from asexual reproductions carried out in The Netherlands. Data was collected on two-year-old plants grown outdoors in The Netherlands in September 2020. The range of day temperatures was 18° C. to 34° C. and the range of night temperatures was 10° C. to 20° C. Plants were pinched/pruned three times. Color references are to The R.H.S. Colour Chart of The Royal Horticultural Society of London (R.H.S.), $6^{th}$ edition (2015).

Classification:

*Family.*—Rosaceae.
*Botanical.*—*Prunus laurocerasus.*
*Common.*—Cherry laurel; English laurel.
*Designation.*—'Zsófi'.

Plant:

*Type.*—Perennial, evergreen shrub.
*Time to produce a finished plant.*—About 2 years from rooted cuttings.
*Appropriate container for producing a finished plant.*—17 cm pots and larger or field-grown.
*Plant shape.*—Broad obovate to spreading upright.
*Growth habit.*—Broad upright.
*Average plant height.*—41.5 cm.
*Average plant diameter.*—36.0 cm.
*Growth rate.*—Low to moderate; about 35 cm per season as a pot-grown young plant.
*Vigor.*—Moderate.
*High temperature tolerance.*—Unknown, but tolerant to temperatures up to 40° C.
*Low temperature tolerance.*—Unknown, but at least hardy to USDA Zone 6.
*Disease/pest resistance and susceptibility.*—Unknown.

Branches:

*Habit*.—Main stems grow from the base and near the base, with lateral branches.

*Basal branching*.—Present.

*Pinching*.—Not required but will improve branching.

*Number of branches per plant*.—Average of 2 main branches and 27 lateral branches per plant; the botanical characteristics are the same as for both the main and lateral branches.

*Branch length* (*both main and lateral*).—Average is 24.7 cm.

*Branch diameter* (*both main and lateral*).—Average is 0.3 cm.

*Internode length* (*both main and lateral*).—Average is 1.3 cm.

*Appearance and shape*.—Rounded and slightly glossy.

*Aspect*.—Average angle of 45 degrees.

*Strength*.—Strong.

*Color*.—Younger branches are in-between RHS 143C (Green) and RHS 144A (Yellow-Green) and fading slightly darker when maturing, in-between RHS 143B (Green) and RHS 144A (Yellow-Green); mature branches are RHS 199B (Grey-brown) with RHS 143A (Green) blotches; color at the internodes is RHS 199B (Grey-brown) with RHS 143A (Green) blotches; color of old stems/bark is RHS 199A (Grey-brown) with fine stripes of RHS 199D (Grey-brown) and lighter.

*Pubescence*.—Absent.

Leaves:

*General*.—At the base of each leaf, there are an average of 3 (varying between 2 and 5) small glands that are visible; the diameter of each gland is 0.075 cm; the color of each gland is RHS 197A (Greyed-Green) but slightly darker; the presence of these glands is typical for this species and the gland shape is oval.

*Arrangement*.—Alternate, single.

*Number of leaves per branch*.—Average is 19.

*Shape*.—Oblanceolate to lanceolate and narrow oblong.

*Aspect*.—Slightly carinate, in an average angle of 45 degrees to the lateral branch.

*Apex*.—Bluntly acute.

*Base*.—Attenuate to acute.

*Margin*.—Coarsely serrate; not lobed.

*Margin undulation*.—Very slight coarsely undulate to non-undulate.

*Length*.—Average is 5.9 cm.

*Width*.—Average is 1.75 cm.

*Texture* (*both upper and lower surface*).—Smooth and glabrous; no pubescence; no rugosity.

*Appearance*.—Upper surface is glossy and lower surface is slightly glossy.

*Venation pattern*.—Pinnate.

*Venation color*.—Upper surface: RHS 144A (Yellow-Green) to RHS 144B (Yellow-Green). Lower surface: RHS 146A (Yellow-Green) to RHS 146B ((Yellow-Green).

*Color*.—Immature: Upper surface: Between RHS 146A (Yellow-Green) and RHS 146B (Yellow-green). Lower surface: Between RHS 144A (Yellow-green) and RHS 146B (Yellow-green). Mature: Upper surface: Between RHS N139A (Green) to RHS 147A (Yellow-green), but slightly darker. Lower surface: RHS 147B (Yellow-green).

*Petiole*.—Length: Average is 0.7 cm. Diameter: Average is 0.15 cm. Color: RHS 144A (Yellow-green). Texture: Smooth and glabrous. Appearance: Upper part is slightly glossy and lower part is glossy. Strength: High. Stipules: Present on both sides of the petiole; shape is linear; length is 0.4 cm; width is 0.075 cm; apex is acute; margin is serrate; color is RHS 147D (Yellow-Green).

*Durability of foliage to stresses*.—Medium.

*Fragrance*.—Typical of species.

Flowers/seed/fruit: Not observed to date.

COMPARISON WITH COMMERCIAL VARIETY

'Zsófi' can be distinguished between the commercial variety 'Antonius' (U.S. Plant Pat. No. 26,314) in Table 1.

TABLE 1

Comparison with Commercial Variety

| Characteristic | 'Zsófi' | 'Antonius' |
|---|---|---|
| Internode length | 1.3 cm | 8.0 cm |

I claim:

1. A new and distinct variety of *Prunus laurocerasus* plant designated 'Zsófi' as illustrated and described herein.

* * * * *